US011298221B2

United States Patent
McCulloch

(10) Patent No.: US 11,298,221 B2
(45) Date of Patent: Apr. 12, 2022

(54) THREE-LENS INTRAOCULAR LENS SYSTEM

(71) Applicant: ALCON INC., Fribourg (CH)

(72) Inventor: Philip Matthew McCulloch, Mansfield, TX (US)

(73) Assignee: Alcon Inc., Fribourg (CH)

(*) Notice: Subject to any disclaimer, the term of this patent is extended or adjusted under 35 U.S.C. 154(b) by 34 days.

(21) Appl. No.: 16/716,111

(22) Filed: Dec. 16, 2019

(65) Prior Publication Data
US 2020/0197165 A1 Jun. 25, 2020

Related U.S. Application Data

(60) Provisional application No. 62/782,811, filed on Dec. 20, 2018.

(51) Int. Cl.
*A61F 2/16* (2006.01)

(52) U.S. Cl.
CPC .......... *A61F 2/1651* (2015.04); *A61F 2/1629* (2013.01); *A61F 2002/16901* (2015.04)

(58) Field of Classification Search
CPC .............. A61F 2/16; A61F 2002/16901; A61F 2/1651; A61F 2/1629; A61F 2002/1682
See application file for complete search history.

(56) References Cited

U.S. PATENT DOCUMENTS

| | | | |
|---|---|---|---|
| 5,196,028 A * | 3/1993 | Portney | A61F 2/16 623/6.35 |
| 5,928,283 A * | 7/1999 | Gross | A61F 2/1651 623/6.34 |
| 7,471,458 B2 | 12/2008 | Straehle | |
| 2002/0120329 A1* | 8/2002 | Lang | A61F 2/1613 623/6.4 |
| 2004/0148023 A1* | 7/2004 | Shu | A61F 2/1629 623/6.34 |
| 2005/0209692 A1* | 9/2005 | Zhang | A61F 2/1648 623/6.34 |
| 2006/0015180 A1* | 1/2006 | Peyman | A61F 2/1602 623/6.36 |
| 2006/0206206 A1* | 9/2006 | Peyman | A61F 2/1651 623/6.34 |
| 2009/0257065 A1* | 10/2009 | Hauger | G02B 21/0012 356/479 |
| 2014/0309734 A1* | 10/2014 | Sohn | A61F 2/1648 623/6.34 |
| 2016/0361157 A1* | 12/2016 | Honigsbaum | A61F 2/1648 |

* cited by examiner

*Primary Examiner* — Yashita Sharma
*Assistant Examiner* — Aren Patel

(57) ABSTRACT

The present disclosure provides a three-lens IOL system including a first, anterior lens, a second, posterior lens rigidly connected to the first lens by at least one rigid member such that the second lens is a fixed distance from the first lens along an axis, a third, center, moveable lens positioned between the first lens and the second lens and adapted to move linearly along the axis anteriorly in a direction of the first lens or posteriorly in a direction of the second lens to change an optical power of the system, and an articulating actuator that contacts the moveable lens and a capsular bag of an eye when the IOL system is implanted in the capsular bag, the articulating actuator adapted to move the moveable lens linearly along the axis.

16 Claims, 3 Drawing Sheets

THREE-LENS INTRAOCULAR LENS SYSTEM

TECHNICAL FIELD

The present disclosure relates to a three-lens intraocular lens (IOL) system, where small, linear movement of a single lens generates a large range of power.

BACKGROUND

The human eye includes a cornea and a crystalline lens that are intended to focus light that enters the pupil of the eye onto the retina. However, the eye may exhibit various refractive errors, which result in light not being properly focused upon the retina, and which may reduce visual acuity. Many interventions have been developed over the years to correct various ocular aberrations. These include spectacles, contact lenses, corneal refractive surgery, such as laser-assisted in situ keratomileusis (LASIK) or corneal implants, and IOLs. IOLs are also used to treat cataracts by replacing the natural diseased crystalline lens of the eye of a patient. During typical IOL-placement surgery, an IOL is inserted into the capsular bag of a patient to replace the natural crystalline lens.

SUMMARY

The present disclosure provides a three-lens IOL system including a first, anterior lens, a second, posterior lens rigidly connected to the first lens by at least one rigid member such that the second lens is a fixed distance from the first lens along an axis, a third, center, moveable lens positioned between the first lens and the second lens and adapted to move linearly along the axis anteriorly in a direction of the first lens or posteriorly in a direction of the second lens to change an optical power of the system, and an articulating actuator that contacts the moveable lens and a capsular bag of an eye when the IOL system is implanted in the capsular bag, the articulating actuator adapted to move the moveable lens linearly along the axis.

The three-lens IOL system may also include one or more of the following additional features, which may be combinable with one another and with other features of this disclosure in any and all combination, unless clearly mutually exclusive:

i) the articulating actuator may include a lever point, a first arm located between the lever point and the moveable lens and adapted to contact the moveable lens, a contact adapted to contact an interior surface of the capsular bag when the IOL system is implanted in the eye, and a second arm located between the contact and the lever point, wherein the first and second arm form an angle $\theta$;

ii) the first lens may have a positive focal length, the second lens may have a negative focal length, and the moveable lens may have a positive focal length;

iii) the first lens may have a first focal length, the second lens may have a second focal length, and the third moveable lens may have a third focal length and the optical power of the system may be a function of the first focal length, the second focal length, and the third focal length, a nominal system optical power, and a nominal distance $t1$ between a center of the moveable lens and the first lens along the axis;

iv) the first focal length may be between 18 mm and 28 mm, inclusive, the second focal length may be between −4.5 mm and −8.5 mm, inclusive, and the third focal length may be between 5 mm and 15 mm, inclusive;

v) the distance d may be between 3.00 mm and 6.00 mm, inclusive; vi) the optical power of the IOL system may have a range of between 6 diopters and 34 diopters, inclusive;

vii) a distance $t1$ between the center of the moveable lens and the first lens along the axis may change by between 0.1 mm and 0.3 mm, inclusive, in response to a movement of the articulating actuator;

viii) the articulating actuator may be adapted to move the moveable lens posteriorly toward the second lens when the capsular bag contracts;

ix) the articulating actuator may be configured to move the moveable lens anteriorly toward the first lens when the capsular bag relaxes;

x) the articulating actuator may be adapted such that the first arm pivots around the lever point to form a more acute angle with the second arm when the capsular bag tightens and to move the moveable lens posteriorly towards the second lens as a result;

xi) the articulating actuator may be adapted such that the first arm pivots around the lever point to form a more obtuse angle with the second arm when the capsular bag relaxes and to move the moveable lens anteriorly towards the first lens as a result.

BRIEF DESCRIPTION OF THE DRAWINGS

For a more complete understanding of the present disclosure, reference is now made to the following description, taken in conjunction with the accompanying drawings illustrating aspects of the present disclosure, in which like components have like numerals, including with alphabetic designations of variants, such as 10a, 10b, and in which.

DETAILED DESCRIPTION

The present disclosure relates to a three-lens accommodating IOL system in which the three lenses are aligned in series with one another. The system can use small, linear movements of a single lens to generate a large range of power.

The IOL system is configured to be placed inside of a capsular bag in an eye. The IOL system includes a first lens and a second lens that are rigidly connected and have a fixed distance from one another. The IOL system further includes a third, center, moveable lens located between the first lens and the second lens. The moveable lens is adapted to move linearly posteriorly or anteriorly between the first and second lenses. When the moveable lens is at a posterior position, the optical power of the IOL system is at one end of the range of power, which is useful for distance viewing. When the moveable lens is at an anterior position, the optical power of the IOL system is at the other end of the range of power, which is useful for near viewing. The small, linear movement of the moveable lens may generate a large change in optical power, providing a larger range of power than is achievable with conventional IOLs.

In addition, the moveable lens may be moved in response to natural eye responses. The moveable lens is in contact with an articulating actuator, which is in contact with the capsular bag of the eye. The capsular bag tightens and relaxes in response to ciliary muscle movements in the eye. These ciliary muscle movements occur naturally as a response to the distance of an object from the eye, as the brain attempts to focus the eye on the object. When the capsular bag is taught, this force from the capsular bag applies force to the moveable lens through an articulating actuator. This force pushes the lens to a posterior position for distance viewing. When the capsular bag is relaxed, the articulating actuator is not engaged or is less engaged than when the capsular bag is taught. The absence of force on the moveable lens, when the capsular bag is in a relaxed state, brings the moveable lens to an anterior position for near viewing.

The first, second, and moveable lenses herein may correspond to "optics" in conventional IOLs.

Figure 1A:
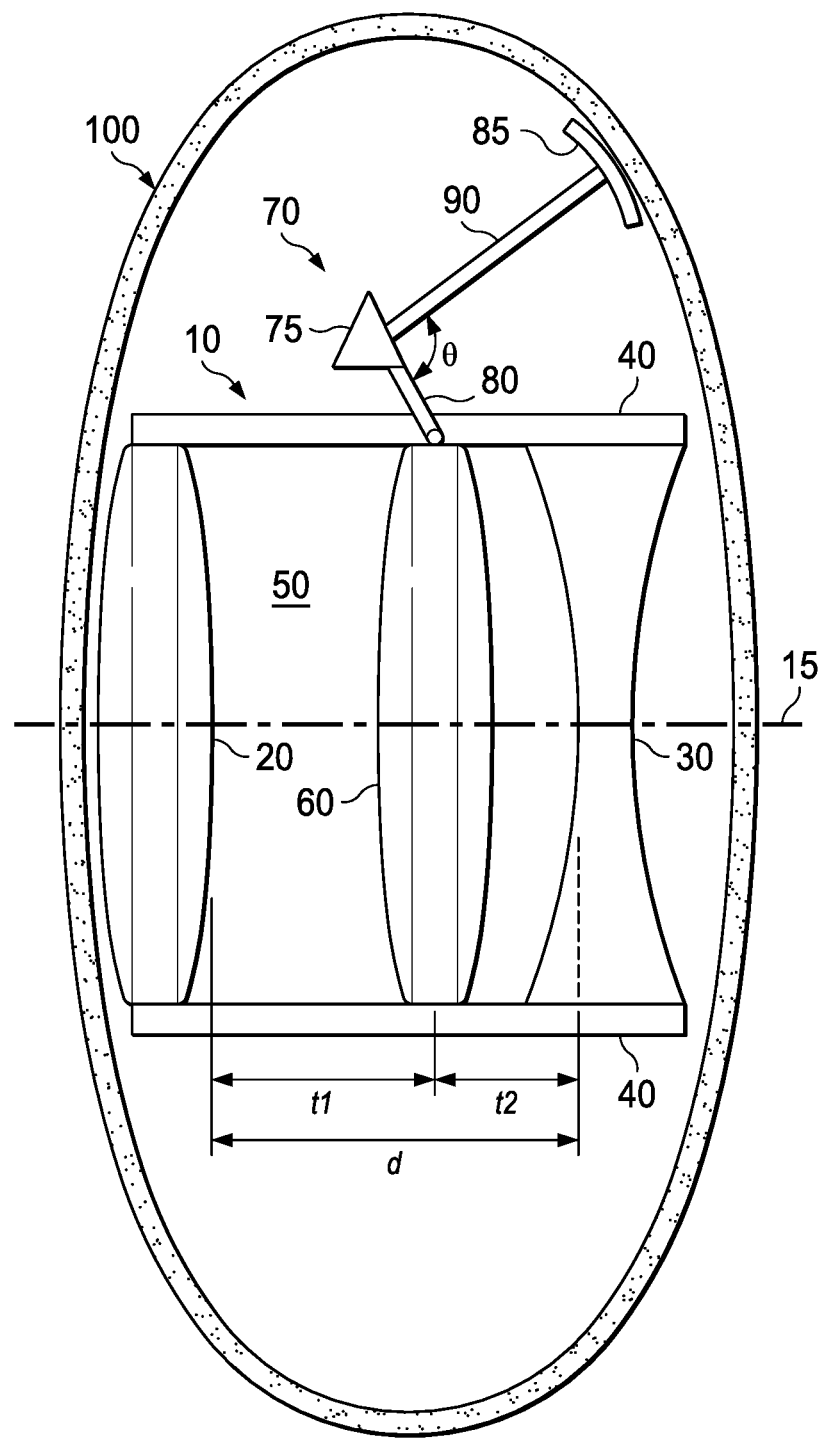
FIG. 1A is a schematic side view diagram of a three-lens IOL system in a contracted capsular bag of an eye with a central, moveable lens in a posterior position.
Figure 1B:
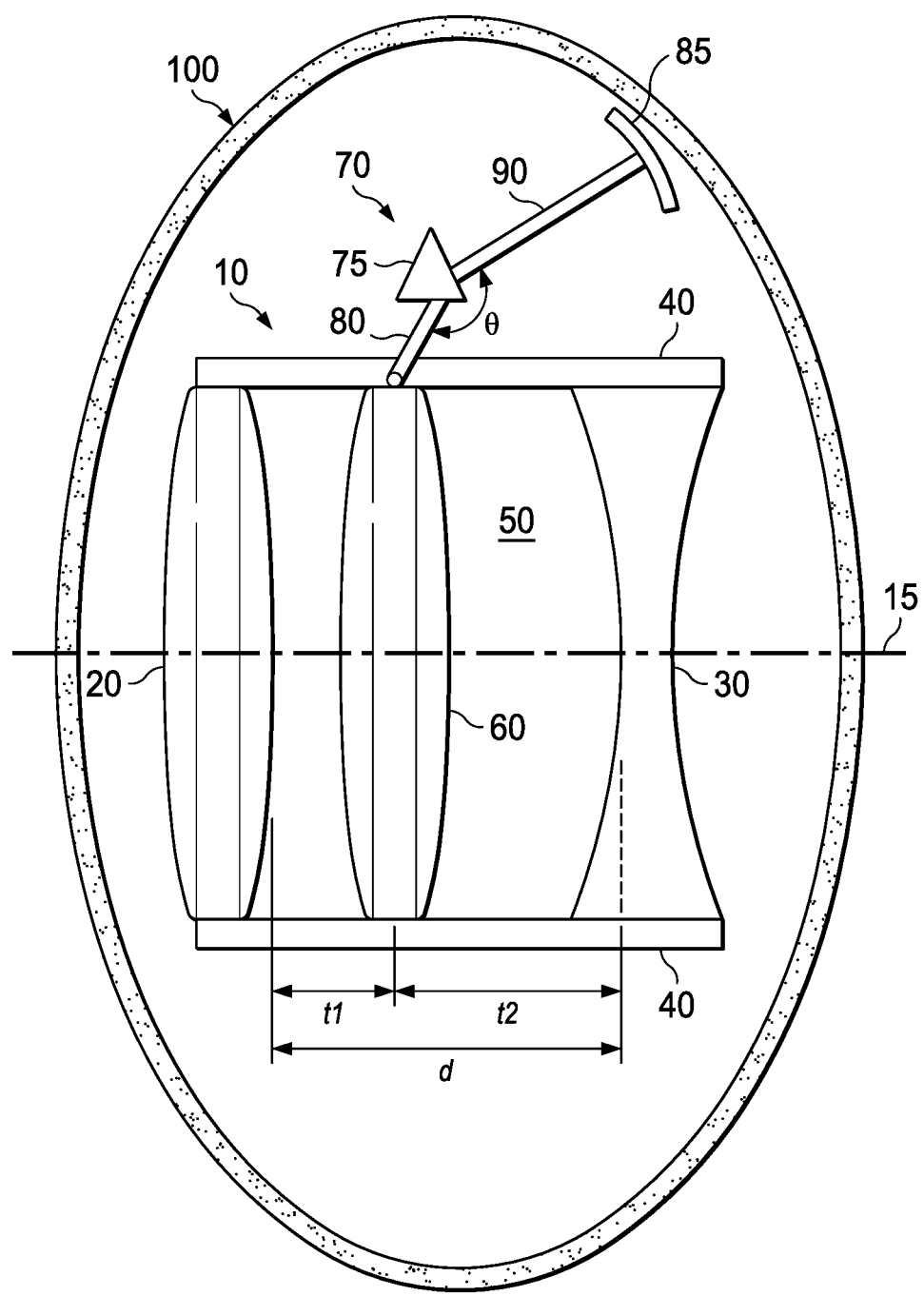
FIG. 1B is a schematic side view diagram of a three-lens IOL system in a relaxed capsular bag of an eye, with a central, moveable lens in an anterior position.

Referring to FIGS. 1A-1B, a three-lens IOL system 10 is shown inside of a capsular bag 100 in an eye. The three-lens IOL system 10 includes a first, anterior lens 20 rigidly connected to a second, posterior lens 30 by at least one rigid member 40. Although only two small rigid members 40 are depicted in FIGS. 1A and 1B for simplicity, a plurality of rigid members 40 may be present, which may largely enclose a cavity 50 between the first lens 20 and the second lens 30 with the exception of passages for the articulating actuator 70. Alternatively, rigid members 40 may be few in number, for example two, but be much larger than depicted such that they largely enclose the cavity 50 with the exception of passages for the articulating actuator 70.

The rigid member 40 rigidly connect the first lens 20 and the second lens 30 and establish a fixed distance, d, between the first lens 20 and the second lens 30 along axis 15. In some examples, this fixed distance, d, may be between 3.00 mm and 6.00 mm, inclusive, between 3.25 mm and 3.65 mm, inclusive, between 3.60 mm and 3.70 mm, inclusive, 3.65 mm, or 3.25 mm. Axis 15 may be perpendicular to the center surfaces of the first lens 20 and the second lens 30.

A third, center, moveable lens 60 is positioned in the cavity 50 between the first lens 20 and the second lens 30. The rigid members 40 may help retain the moveable lens 60 in this location. The moveable lens 60 is adapted to move linearly along axis 15 anteriorly in the direction of the first lens 20 or posteriorly in the direction of the second lens 30. The axis 15 may also be perpendicular to the center surfaces of the moveable lens 60.

The distance d is a total of a distance t1 between the first lens 20 and the center of the moveable lens 60 along axis 15, and a distance t1 between the second lens 30 and the center of the moveable lens 60 along axis 15. Although t1 and t2 may change depending on the location of the moveable lens 60, the total distance d is fixed.

The rigid member 40 may, in some examples (not shown), include a track and a moveable coupling located within the track and connected to the moveable lens 60 to allow the moveable lens 60 to move linearly along the axis 15, while still remaining properly oriented with respect to the first lens 20 and the second lens 30.

In other examples, the moveable lens 60 may make contact with the track, for example via at least three points around its perimeter, instead of being mechanically fixed to the track via a moveable coupling.

The three-lens IOL system 10 also includes at least one articulating actuator 70 in contact with the moveable lens 60. In some examples, the articulating actuator 70 may be fixedly attached to the moveable lens 60. The articulating actuator 70 includes a lever point 75 and a first arm 80 located between the lever point 75 and the moveable lens 60. The first arm 80 may form a continuous molded part with the moveable lens 60. The junction between the first arm 80 and the moveable lens 60 may be a flexure to facilitate the translation of forces on the capsular bag to movement of the moveable lens 60. The articulating actuator 70 also includes a contact 85 that contacts or is located near the interior surface of the capsular bag 100 (depending, typically, on whether the capsular bag 100 is relaxed or contracted), and a second arm 90 located between the contact 85 and the lever point 75. The contact may be an annular ring (not shown), which may be in contact with the anterior or posterior surface of the capsular bag 100. Moveable lens 60 may contact the annular ring at multiple points. The annular ring may cantilever the movement of the moveable lens 60 with respect to the bag using flexures with the arms. The articulating actuator 70 may enter the cavity 50 via a passage in the rigid members 40, which may help keep articulating actuator 70 in position.

The contact 85 may be a pad or small member as shown, or it may simply be an end of the second arm 90. In some examples, the contact 85 may have a smooth surface, a curved shape, or both to facilitate movement against the capsular bag 100 without damaging the capsular bag.

Although only one articulating actuator 70 is shown in FIGS. 1A-1B for simplicity, it is possible for the three-lens IOL system 10 to include a second articulating actuator 70 on its opposite side.

The capsular bag 100 is a natural piece of eye anatomy which interfaces with ciliary muscles to impart pressure on the natural lens to provide accommodation. When the capsular bag 100 is contracted, as seen in FIG. 1A, it applies force to the contact 85 of the articulating actuator 70, which causes the first arm 80 to pivot around the lever point 75 from a more acute angle θ with respect to the second arm 90 than if the capsular bag 100 were relaxed. This moves the moveable lens 60 to a posterior position for distance viewing. The distance t1 between the first lens 20 and the moveable lens 60 when the moveable lens 60 is in the posterior position may be between 1 mm and 2.5 mm, inclusive, or 1.55 mm.

When the capsular bag 100 is relaxed, as seen in FIG. 1B, the capsular bag 100 applies no force to the contact 85, or less force than when the capsular bag 100 is contracted, which causes the first arm 80 to pivot around lever point 75 to form a less acute angle θ (not shown), or even an obtuse angle θ as depicted with respect to the second arm 90 than if the capsular bag 100 were contracted. This moves the moveable lens 60 to an anterior position for near viewing. The distance t1 between the first lens 20 and the moveable lens 60 when the moveable lens 60 is in the anterior position may be between 1 mm and 2.5 mm, inclusive, or 1.20 mm.

In some examples, t1 may change by between 0.05 mm and 0.4 mm, inclusive, or between 0.1 and 0.3 mm, inclusive in response to the articulating actuator 70.

The articulating actuator 70 amplifies small changes in position of the capsular bag 100 to cause changes in the optical power of the three-lens IOL system 10.

A change in position of the moveable lens 30 along axis 15 changes the focal length and resulting optical power of the IOL system 10. The balance of positive and negative powers among the lenses creates a non-linear response in focal length to the shift in position of the moveable lens 60. The derivation focal length for the IOL system 10 is a function of the distance t1 between the moveable lens 60 and the first lens 20. A change in position of the moveable lens 60 alters the effective optical power of the first lens 20 and has an inverse effect on the effective optical power of the second lens 30, according to the following equation:

$$\emptyset_{1m3} = \emptyset_{1m} + \emptyset_2 - \emptyset_{1m}\emptyset_2(d - t_1 + d'_{1m}) \quad \text{(equation 1)}$$

where $\emptyset_{1m3}$ is the optical power of the entire three-lens IOL system 10;

$$\emptyset_{1m3} = \frac{1}{f_{1m3}} = \text{the inverse of the focal length of the three-lens IOL system 10;}$$

$f_{1m3}$ = the focal length of the three-lens IOL system 10;

d = distance between the first lens 20 and the second lens 30 along axis 15;

t1 = distance between first lens 20 and the center of the moveable lens 60 along axis 15;

t2 = d−t1 = distance between the second lens 30 and the moveable lens 60 along axis 15;

$\emptyset_{1m} = \emptyset_1 + \emptyset_m - \emptyset_1\emptyset_m t_1$ = the inverse of the focal length of the combination of first lens 20 and the moveable lens 60;

$\emptyset_{1m}$ is the net optical power of the first lens 20 and the moveable lens 60;

$\emptyset_1$ = the inverse of the focal length of first lens 20;

$\emptyset_m$ = the inverse of the focal length of moveable lens 60;

$\emptyset_2$ = the inverse of the focal length of second lens 30; and $$d'_{1m} = \frac{-\emptyset_1 t_1}{\emptyset_{1m}} = \frac{-\emptyset_1 t_1}{\emptyset_1 + \emptyset_m - \emptyset_1\emptyset_m t_1}.$$

A combination of two lenses, such as the first lens 20 and the moveable lens 60, results in a linear change in the total lens optical power proportional to the change in position of the moveable lens 20 with respect to the first lens 20. The moveable lens 30 increases the range of optical power change obtainable without a large range of available movement distance of the moveable lens 60. Combining variables and equation 1 into a single equation results in the following equation for the combined inverse of the focal length for the three-lens IOL system 10:

$$\emptyset_{1m3} = (\emptyset_1 + \emptyset_m - \emptyset_1\emptyset_m t_1) + \emptyset_2 - (\emptyset_1 + \emptyset_m - \emptyset_1\emptyset_m t_1)\emptyset_2\left(d - t_1 + \frac{-\emptyset_1 t_1}{\emptyset_1 + \emptyset_m - \emptyset_1\emptyset_m t_1}\right)$$

The first lens 20, the second lens 30, and the moveable lens 60 may have lens properties, such as optical power and focal length, and be arranged such that a small change in distance t1 and distance t2 results in a large change in focal length and optical power of the three-lens IOL system 10.

Figure 2:
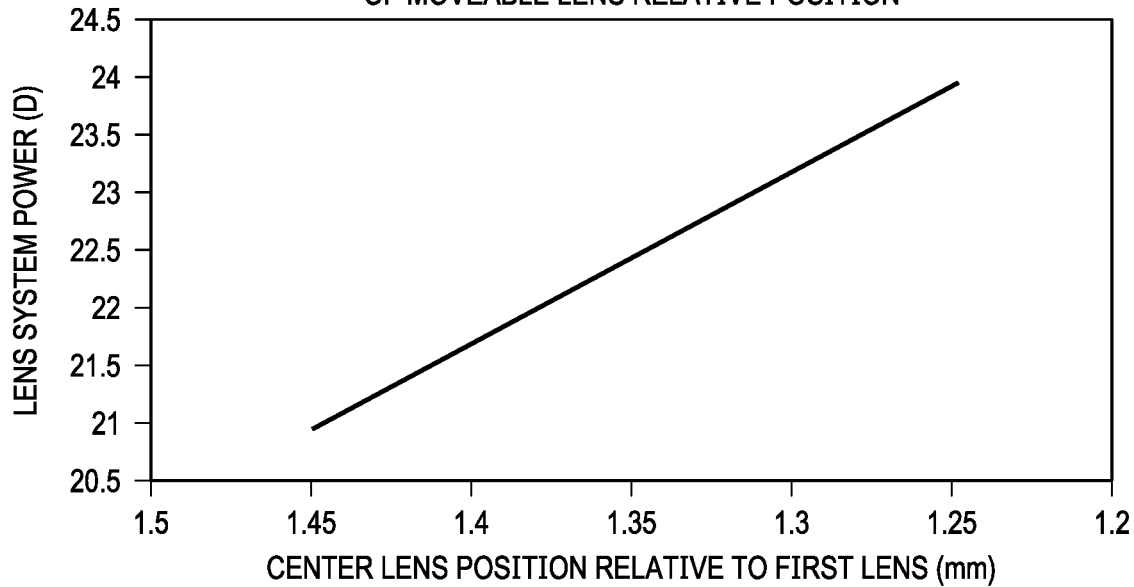
FIG. 2 is an example graph of the relationship between the position of the center, moveable lens relative to the first lens and the lens system optical power.

FIG. 2 is an example graph of the relationship between the distance t1 between the moveable lens 60 relative to the first lens 60 and the optical power of the three-lens IOL system 10.

Choice of distance d, nominal lens power for each of the three lenses, and range of movement of the moveable lens 60 each impact the range of optical power available with the three-lens IOL system 10, the nominal optical power of the three-lens IOL system 10, and sensitivity of the optical power of three-lens IOL system 10 to movement of the moveable lens 60. For an example IOL system, meaningful constraints may include a distance d as discussed above, a nominal optical power of between 20 and 22 diopters, inclusive, or 21 diopters, and a +/−3 diopter change in optical power for a 0.1 mm to 0.3 mm, inclusive, or a 0.2 mm change in t1.

The range of optical power of the IOL system 10 may be between 6 and 34 diopters, inclusive.

For an example three-lens IOL system 10, the following Table 1 shows the individual lens focal lengths, the nominal moveable lens 60 position as expressed by t1, the nominal system optical power (D=diopters), and the change in optical power for a 0.2 mm change in t1. The numbers in Table 1 describe the graph in FIG. 2.

TABLE 1

Nominal Three-Lens IOL System Optical Power and Change in Optical Power as a Function of Lens Focal Length and Position

| Lens | Individual Lens Focal Length (mm) | Nominal System moveable lens position, t1 (mm) | Nominal System Optical Power (D) | Change in Optical Power for a 0.2 mm change in t1 |
|---|---|---|---|---|
| 1st | 23.00 | 1.45 | 20.97 | 2.999 |
| Moveable | 10.00 | | | |
| 2nd | −6.50 | | | |

In general, in the three-lens IOL system 10, the first lens 20 and the moveable lens 60 may both have a positive focal length, while the second lens 30 may have a negative focal length.

In one example, the first lens 20 may have a first focal length of between 18 mm and 28 mm, inclusive. The second lens 30 may have a second focal length between −4.5 mm and −8.5 mm, inclusive. The moveable lens 60 may have a third focal length between 5 mm and 15 mm, inclusive.

Figure 3:
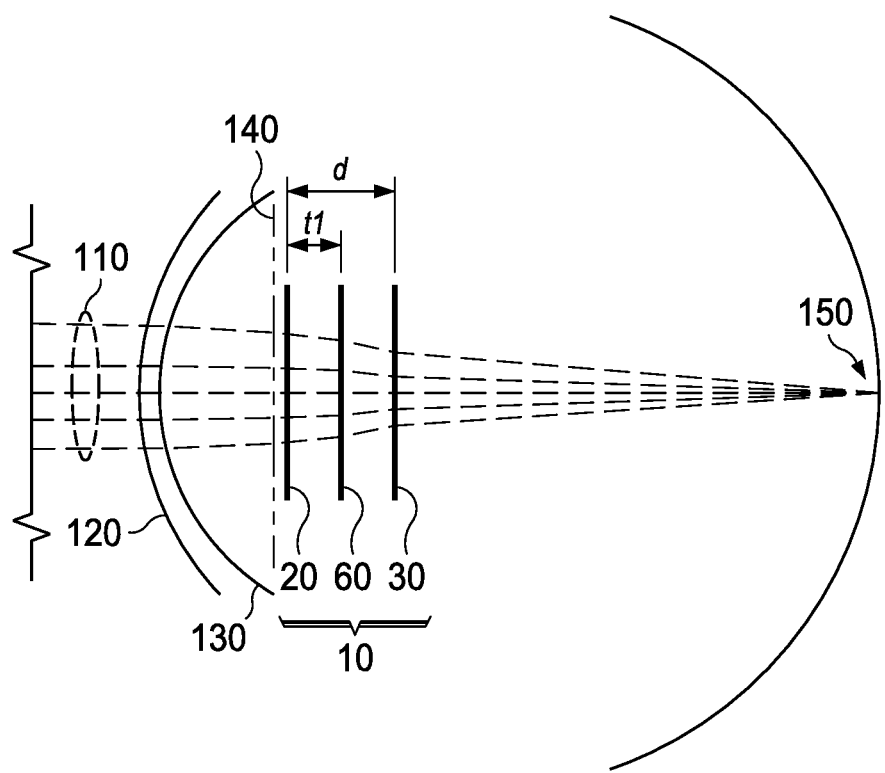
FIG. 3 is a schematic diagram of a model eye with the three-lens IOL system in place.

FIG. 3 is a schematic diagram of a model eye with the three-lens IOL system 10 in place. IOL system 10 includes the first lens 20 in an anterior position of the eye, the second lens 30 in a posterior position of the eye, and the moveable lens 60 between the first lens 20 and the second lens 30. The moveable lens 60 is adapted to move linearly posteriorly or anteriorly between the first lens 20 and second lens 30. In FIG. 3, the relative positions of first lens 20, the moveable lens 60, and the second lens 30 are represented by vertical lines.

Rays of light 110 may pass through the eye, first passing through the first corneal surface 120, then through the second corneal surface 130, then through the pupil plane 140. The IOL system 10 may be positioned posterior to the pupil plane 140. The rays of light may then pass through the first lens 20, followed by the moveable lens 60, then the second lens 30. Finally, the rays of light converge on the retina 150.

When the moveable lens 60 is at a posterior position, the optical power of the IOL system 10 is at one end of the range of power, which is useful for distance viewing. When the moveable lens 60 is at an anterior position, the optical power of the IOL system 10 is at the other end of the range of power, which is useful for near viewing. The small, linear movement of the moveable lens 60 may generate a large change in optical power, providing a larger range of power than is achievable with conventional IOLs.

For example, for an approximately 20 diopter nominally powered IOL system, the first lens may be 31 diopter, the second lens may be −6.5 diopter, and the moveable lens may be 10 diopter. The distance d between the first lens and second lens may be approximately 3.25 mm. For distance viewing, the distance t1 between the first lens and moveable lens may be approximately 1.45 mm. For intermediate viewing, the distance U between the first lens and the moveable lens may be approximately 1.35 mm. For close viewing, the distance t1 between the first lens and the moveable lens may be approximately 1.25 mm.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

The invention claimed is:

1. A three-lens intraocular lens (IOL) system comprising:
a first, anterior lens;
a second, posterior lens rigidly connected to the first lens by at least one rigid member such that the second lens is a fixed distance, d from the first lens along an axis;
a third, center, moveable lens positioned between the first lens and the second lens and adapted to move linearly along the axis anteriorly in a direction of the first lens or posteriorly in a direction of the second lens to change an optical power of the system; and
an articulating actuator that contacts the moveable lens and a capsular bag of an eye when the IOL system is implanted in the capsular bag, the articulating actuator adapted to move the moveable lens linearly along the axis, the articulating actuator comprising:
a lever point;
a first arm located between the lever point and the moveable lens and adapted to contact the moveable lens;
a contact adapted to contact an interior surface of the capsular bag when the IOL system is implanted in the eye; and
a second arm located between the contact and the lever point;
wherein the first and second arms form an angle θ; and
wherein the articulating actuator is adapted such that the first arm pivots around the lever point to form a more obtuse angle with the second arm when the capsular bag relaxes and to move the moveable lens anteriorly towards the first lens as a result.

2. The IOL system of claim 1, wherein:
the first lens has a positive focal length;
the second lens has a negative focal length; and
the moveable lens has a positive focal length.

3. The IOL system of claim 2, wherein the first lens has a first focal length, the second lens has a second focal length, and the moveable lens has a third focal length; wherein the optical power of the system is a function of the first focal length, the second focal length, and the third focal length; a nominal system optical power; and a nominal distance t1 between a center of the moveable lens and the first lens along the axis.

4. The IOL system of claim 3, wherein the first focal length is between 18 mm and 28 mm, inclusive, the second focal length is between −4.5 mm and −8.5 mm, inclusive, and the third focal length is between 5 mm and 15 mm, inclusive.

5. The IOL system of claim 1, wherein the distance d is between 3.00 mm and 6.00 mm, inclusive.

6. The IOL system of claim 1, wherein the optical power of the IOL system has a range of between 6 diopters and 34 diopters, inclusive.

7. The IOL system of claim 1, wherein a distance t1 between the center of the moveable lens and the first lens along the axis changes by between 0.1 mm and 0.3 mm, inclusive, in response to a movement of the articulating actuator.

8. The IOL system of claim 1, wherein the articulating actuator is adapted to move the moveable lens posteriorly toward the second lens when the capsular bag contracts.

9. A three-lens intraocular lens (IOL) system, comprising:
a first, anterior lens;
a second, posterior lens rigidly connected to the first lens by at least one rigid member such that the second lens is a fixed distance, d from the first lens along an axis;
a third, center, moveable lens positioned between the first lens and the second lens and adapted to move linearly along the axis anteriorly in a direction of the first lens or posteriorly in a direction of the second lens to change an optical power of the system; and
an articulating actuator that contacts the moveable lens and a capsular bag of an eye when the IOL system is implanted in the capsular bag, the articulating actuator adapted to move the moveable lens linearly along the axis;
wherein a distance t1 between the center of the moveable lens and the first lens along the axis changes by between 0.1 mm and 0.3 mm, inclusive, in response to a movement of the articulating actuator.

10. The IOL system of claim 9, wherein:
the first lens has a positive focal length;
the second lens has a negative focal length; and
the moveable lens has a positive focal length.

11. The IOL system of claim 9, wherein the distance d is between 3.00 mm and 6.00 mm, inclusive.

12. The IOL system of claim 9, wherein the optical power of the IOL system has a range of between 6 diopters and 34 diopters, inclusive.

13. The IOL system of claim 9, wherein the articulating actuator comprises:
a lever point;
a first arm located between the lever point and the moveable lens and adapted to contact the moveable lens;
a contact adapted to contact an interior surface of the capsular bag when the IOL system is implanted in the eye;
a second arm located between the contact and the lever point,
wherein the first and second arm form an angle θ.

14. A three-lens intraocular lens (IOL) system, comprising:
a first, anterior lens;
a second, posterior lens rigidly connected to the first lens by at least one rigid member such that the second lens is a fixed distance, d from the first lens along an axis;
a third, center, moveable lens positioned between the first lens and the second lens and adapted to move linearly along the axis anteriorly in a direction of the first lens or posteriorly in a direction of the second lens to change an optical power of the system; and
an articulating actuator that contacts the moveable lens and a capsular bag of an eye when the IOL system is implanted in the capsular bag, the articulating actuator adapted to move the moveable lens linearly along the axis, the articulating actuator comprising:

a lever point;

a first arm located between the lever point and the moveable lens and adapted to contact the moveable lens;

a contact adapted to contact an interior surface of the capsular bag when the IOL system is implanted in the eye; and a second arm located between the contact and the lever point;

wherein the first and second arm form an angle $\theta$; and wherein the articulating actuator is adapted such that the first arm pivots around the lever point to form a more acute angle with the second arm when the capsular bag tightens and to move the moveable lens posteriorly towards the second lens as a result.

15. The IOL system of claim 14, wherein the articulating actuator is further adapted such that the first arm pivots around the lever to form a more obtuse angle with the second arm when the capsular bag relaxes and to move the moveable lens anteriorly towards the first lens as a result.

16. The IOL system of claim 14, wherein the distance d is between 3.00 mm and 6.00 mm, inclusive.

* * * * *